United States Patent

Schnaibel et al.

[11] Patent Number: 6,034,610
[45] Date of Patent: Mar. 7, 2000

[54] METHOD AND ARRANGEMENT FOR MONITORING THE OPERATION OF A GAS PROBE

[75] Inventors: Eberhard Schnaibel, Hemmingen; Erich Junginger, Stuttgart; Lothar Raff, Remseck, all of Germany

[73] Assignee: Robert Bosch GmbH, Stuttgart, Germany

[21] Appl. No.: 09/114,483

[22] Filed: Jul. 13, 1998

[30] Foreign Application Priority Data

Jul. 11, 1997 [DE] Germany ............. 197 29 696

[51] Int. Cl.[7] ............................................. G08B 21/00
[52] U.S. Cl. ................. 340/635; 340/438; 123/679; 123/697; 123/690; 73/23.31
[58] Field of Search ................. 340/635, 449, 340/438, 450.2, 620, 622, 632, 633, 634; 123/679, 688, 690, 697; 73/25.01, 25.02, 25.03, 23.3; 338/28, 34; 204/401

[56] References Cited

U.S. PATENT DOCUMENTS

| | | |
|---|---|---|
| 5,090,387 | 2/1992 | Mayer et al. . |
| 5,228,426 | 7/1993 | Pursifull et al. . |
| 5,245,979 | 9/1993 | Purisfull et al. . |
| 5,285,762 | 2/1994 | Werner et al. ................. 123/697 |
| 5,311,138 | 5/1994 | Ott et al. . |
| 5,392,643 | 2/1995 | O'Kennedy et al. . |
| 5,616,835 | 4/1997 | Schnaibel et al. ............. 123/697 |
| 5,898,107 | 4/1999 | Schenk ................................ 73/118.1 |

*Primary Examiner*—Jeffrey A. Hofsass
*Assistant Examiner*—Anh La
*Attorney, Agent, or Firm*—Walter Ottesen

[57] ABSTRACT

The invention is directed to a method for monitoring the operation of a gas probe, such as a λ-probe for an internal combustion engine. The λ-probe has a probe ceramic (Nernst cell) and a probe heater. The internal resistance (x) of the probe ceramic is measured and a desired value (y) is determined in dependence upon the temperature of the gas to be detected and the heating power of the probe heater. The internal resistance (x) is then compared to the desired value (y) and, when the measured value of the internal resistance (x) exceeds the desired value (y), then a fault signal is generated and/or the fault signal is outputted and/or the fault signal is stored.

5 Claims, 1 Drawing Sheet

METHOD AND ARRANGEMENT FOR MONITORING THE OPERATION OF A GAS PROBE

FIELD OF THE INVENTION

The invention relates to a method for monitoring the operation of a gas probe such as a λ-probe for an internal combustion engine. The λ-probe includes a probe ceramic (Nernst cell) for detecting gas molecules and a probe heater.

BACKGROUND OF THE INVENTION

Control methods and control arrangements are known which receive their control variable from a gas probe mounted in the exhaust-gas system of the engine. In this way, a specific air/fuel ratio of the air/fuel mixture supplied to the engine is maintained. The gas probes can, for example, be a λ-probe or an HC probe. This control is, in general, superposed on a mixture control arrangement with which the composition of the air/fuel mixture is coarsely precontrolled. The precondition for a trouble free operation of such a control unit is that the gas probe operates free of trouble.

According to the regulations of California as well in accordance with United States Federal regulations, the function of all exhaust-gas relevant components of an internal combustion engine, such as injection systems, catalatic converters and the like, must be monitored during the operation utilizing on-board equipment (on-board diagnosis OBD). The operational readiness for most known gas probes is ensured only at a specific operating temperature. These gas probes include, for example, λ-probes or HC probes.

For the above reason, probe heaters are provided in such gas probes of the Nernst type. The probe heaters additionally heat the probes during the cold-start and warm-up phase of the engine so that the required operating temperature is reached earlier. The function of the exhaust-gas probe (that is, the function of the Nernst cell as well as the function of the probe heater) are exhaust-gas relevant quantities. For this reason, the monitoring thereof is required in the context of the on-board diagnosis.

U.S. Pat. No. 5,090,387 discloses, for example, a method and an arrangement for checking the operability of an exhaust-gas probe heater and its feed-line system. This method and arrangement permit monitoring the probe heater without additional sensors or lines.

It is problematic with this method and arrangement that only the probe heater can be monitored but not the operation of the probe itself.

U.S. Pat. No. 5,311,138 discloses an arrangement for monitoring the operation of the following: an electric/electronic switch (output stage), a consumer connected to the switch; the drive and the connecting lines of the switch, which, for example, can be utilized also for monitoring the probe heater. However, this arrangement, too, only permits monitoring the probe heater but does not permit monitoring the actual probe itself.

SUMMARY OF THE INVENTION

It is an object of the invention to provide a method and an arrangement for monitoring the operation of a gas probe such as a λ-probe for an internal combustion engine. It is a further object of the invention to provide such a method and an arrangement which are further improved so that it is not only possible to monitor the probe heater but that they also permit monitoring the probe ceramic for detecting gas molecules, that is, the Nernst cell, and to perform this monitoring in a simple manner.

The method of the invention is for monitoring the operation of a gas probe such as a λ-probe for an internal combustion engine. The λ-probe has a probe ceramic (Nernst cell) and a probe heater. The method includes the steps of: measuring the internal resistance (x) of the probe ceramic; providing a desired value (y) determined in dependence upon the temperature of the gas to be detected and the heating power of the probe heater; comparing the internal resistance (x) to the desired value (y); and, when the measured value of the internal resistance (x) exceeds the desired value (y), then generating a fault signal and/or outputting the fault signal and/or storing the fault signal.

The above method affords the special advantage that the Nernst cell is monitored without additional sensors because only the internal resistance of the probe ceramic is detected and must be compared to a desired value of the internal resistance. This desired value is determined in dependence upon the temperature of the gas to be detected and the heater power of the probe heater. The temperature of the engine is anyway detected.

The detection of the internal resistance can, for example, be made with an arrangement disclosed in U.S. patent application Ser. No. 09/923,966, filed Sep. 5, 1997, and incorporated herein by reference.

In principle, the above-described monitoring of the internal resistance of the gas probe is adequate for the monitoring of its function because, on the one hand, the operability of the Nernst cell is detected by detecting the internal resistance while, on the other hand, the operability of the probe heater can be detected during the cold-start phase or the warm-up phase because a proper operation of the gas probe in the cold-start phase or warm-up phase has, perforce, an operational probe heater.

An especially advantageous embodiment of the method provides however that, in combination with the detection of the internal resistance of the probe ceramic, the probe heater is monitored for the occurrence of one or more of the following faults: short circuit to positive potential, load drop, short circuit to ground. Furthermore, a fault signal is generated and/or outputted and/or stored when one or more of the above mentioned faults occur, namely: short circuit to positive potential, load drop and short circuit to ground.

The arrangement of the invention is for monitoring the operation of a gas probe, such as a λ-probe for an internal combustion engine. The λ-probe has a probe ceramic (Nernst cell) and a probe heater. The arrangement includes the following: means for detecting the temperature of the gas to be detected; means for detecting the heating power of the probe heater; means for computing a desired value (y) of the internal resistance of the probe ceramic in dependence upon the temperature of the gas to be detected and the heating power; means for measuring the internal resistance of the probe ceramic; means for comparing the computed desired value (y) to the measured internal resistance (x); and, means for outputting and/or storing and/or displaying a fault when the comparison shows a deviation by a pregiven value.

In an advantageous embodiment, a fault detection logic is provided which is connected in parallel to the probe heater output stage. This fault detection logic detects a short circuit to positive potential or a drop in load or a short circuit to ground and, when such a fault is present, a fault signal is generated and/or indicated and/or stored.

BRIEF DESCRIPTION OF THE DRAWINGS

The invention will now be described with reference to the single figure (FIG. 1) of the drawing which is a schematic of an arrangement of the invention for monitoring the operation of a λprobe of an internal combustion engine.

DESCRIPTION OF THE PREFERRED EMBODIMENTS OF THE INVENTION

Figure 1:
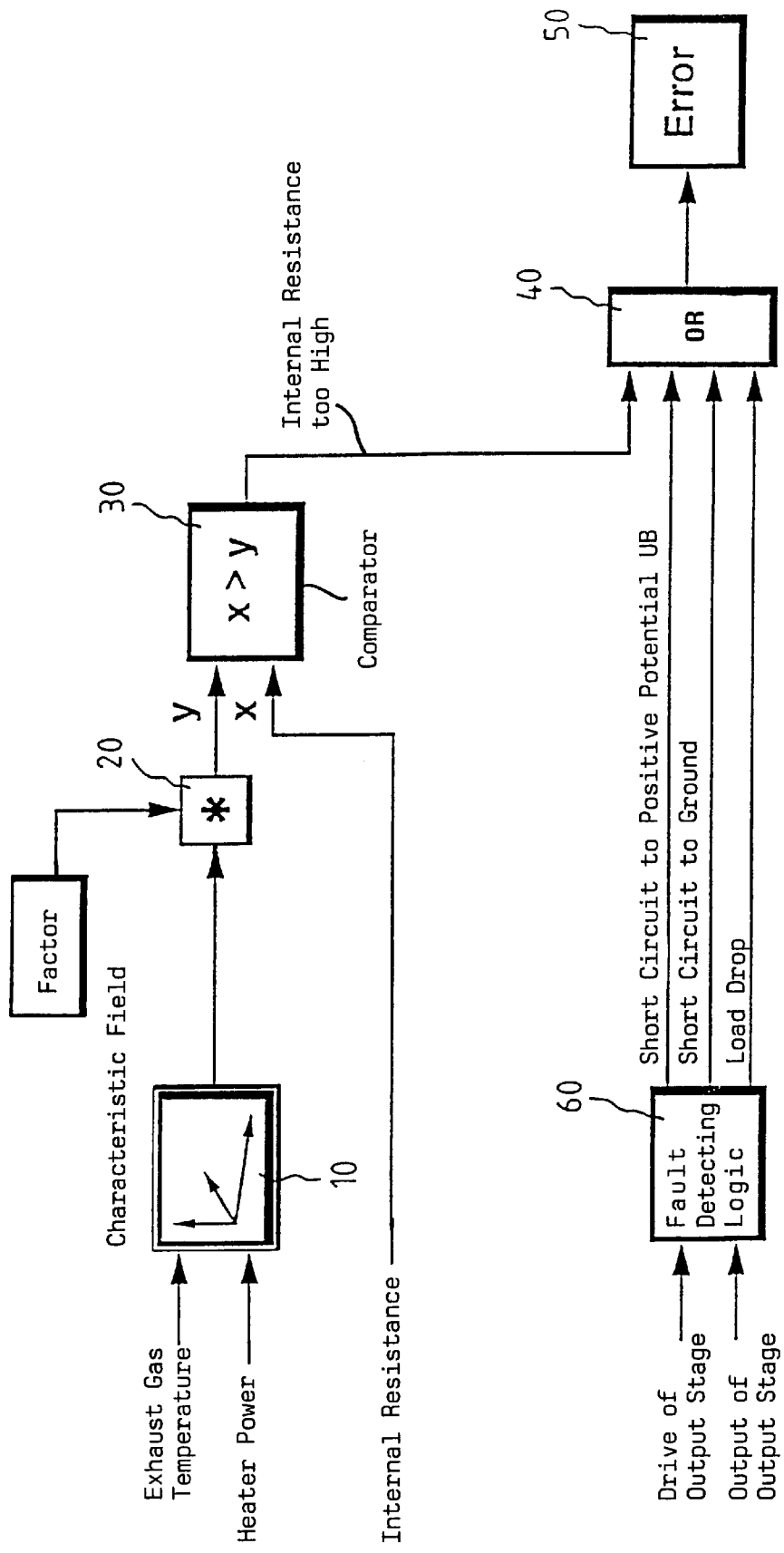

The basic idea of the invention comprises that the operation of a gas probe is monitored by detecting the internal resistance and to make a comparison to an internal-resistance desired value and, when there is a deviation, drawing a conclusion as to a fault. The gas probe is especially a λ-probe for an internal combustion engine and the desired value of the internal resistance is mathematically determined in dependence upon the exhaust-gas temperature and the heater power of the probe heater.

Before the invention is described in detail it should be noted that the block circuit diagram shown in FIG. 1 does not limit the invention but serves especially to make clear the basic operation of the invention and the special operational sequence in a realizable form. The individual blocks can be configured in analog, digital or hybrid form. Furthermore, it is also possible that the blocks can include, for example, microcomputers, microprocessors, digital or analog logic circuits and the like.

The invention is also not limited to the monitoring of the operability of a λ-probe. Rather, the invention can be applied to any desired gas sensor which has a Nernst cell and a probe heater. The method and arrangement for monitoring the operation of a λ-probe of an internal combustion engine will now be described with respect to FIG. 1.

As shown in FIG. 1, the exhaust-gas temperature, the heater power and the internal resistance of the probe ceramic, that is, the Nernst cell of the λ-probe, are detected. An internal resistance of the λ-probe is taken from a characteristic field 10 in dependence upon the exhaust-gas temperature and the heater power. In order to preclude possible errors, the internal resistance so computed is multiplied by a factor which has a magnitude in the order of 2 to 15 and is preferably between 5 to 10. Multiplication takes place in multiplication element 20 and the result, a desired value y, is supplied to a comparator 30. The measured internal resistance (x) is also supplied to this comparator 30.

A comparison is made to determine whether the measured internal resistance (x) is greater than the computed internal resistance (y). If this is the case, a fault signal is supplied to an OR-element 40 which generates a fault signal 50 and displays the same and, if required, also stores the same.

Simultaneously hereto, a diagnosis of the output stage of the probe heater takes place. For this purpose, a fault detecting logic 60 is connected in parallel to the probe heater output stage, that is, the logic 60 is connected between the drive and the output of the probe heater output stage. The fault detecting logic 60 detects a short circuit to the positive potential UB and/or a drop in load which can occur, for example, because of a cable break, and/or a short circuit to ground. The fault detected is supplied to the OR-element 40. When a fault of this kind is present, the fault signal 50 is outputted and displayed and, if required, stored.

The fault detecting logic 60 can, for example, be configured as disclosed in U.S. Pat. No. 5,311,138, incorporated herein by reference.

The essence of the above-described method and the above-described arrangement for monitoring the operation of a λ-probe is that the operability of the λ-probe is detected without additional sensor means by detecting the internal resistance of the probe ceramic, on the one hand, and monitoring the probe heater in combination therewith, on the other hand. It is therefore possible to monitor the operability of the λ-probe independently of the operation of the probe heater. At the same time, a monitoring of the probe heater is effected indirectly via the monitoring of the operability of the probe because a λ-probe only functions properly in the cold-start phase or warm-up phase when a proper operation of the probe heater is provided.

It is understood that the foregoing description is that of the preferred embodiments of the invention and that various changes and modifications may be made thereto without departing from the spirit and scope of the invention as defined in the appended claims.

What is claimed is:

1. A method for monitoring the operation of a gas probe including a λ-probe for an internal combustion engine, the λ-probe having a probe ceramic (Nernst cell) and a probe heater, the method comprising the steps of:

measuring the internal resistance (x) of said probe ceramic;

providing a desired value (y) determined in dependence upon the temperature of the gas to be detected and the heating power of said probe heater;

comparing said internal resistance (x) to said desired value (y); and, when the measured value of said internal resistance (x) exceeds said desired value (y), then generating a fault signal and/or outputting said fault signal and/or storing said fault signal.

2. The method of claim 1, wherein, in combination with the detection of said internal resistance (x) of said probe ceramic (Nernst cell), said probe heater monitors the occurrence of at least one of the following faults: a short circuit to the positive potential UB, a load drop and a short circuit to ground; and, said probe heater generating a fault signal and/or storing said fault signal and/or outputting said fault signal when at least one of said faults is present.

3. An arrangement for monitoring the operation of a gas probe including a λ-probe for an internal combustion engine, the λ-probe having a probe ceramic (Nernst cell) and a probe heater, the arrangement comprising:

means for detecting the temperature of the gas to be detected;

means for detecting the heating power of the probe heater;

means for computing a desired value (y) of the internal resistance of said probe ceramic in dependence upon the temperature of the gas to be detected and the heating power;

means for measuring said internal resistance of said probe ceramic;

means for comparing the computed desired value (y) to the measured internal resistance (x); and, means for outputting and/or storing and/or displaying a fault when the comparison shows a deviation by a pregiven value.

4. The arrangement of claim 3, further comprising:

said probe heater having an output stage;

a fault detecting logic connected in parallel with said output stage;

said fault detecting logic functioning to detect at least one of the following faults: a short circuit to positive potential (UB), a load drop and a short circuit to ground; and, said fault detecting logic further functioning to generate a fault signal and/or store said fault signal and/or display said fault signal when the fault is present.

5. The arrangement of claim 3, said computing means including a characteristic field having as input quantities: the temperature of the gas to be detected and the heating power; and, said characteristic field having said internal resistance as an output quantity.

* * * * *